US008025627B2

(12) United States Patent
Freeman

(10) Patent No.: US 8,025,627 B2
(45) Date of Patent: Sep. 27, 2011

(54) REUSABLE BIOPSY FORCEPS

(76) Inventor: Ken Freeman, Laconia, NH (US)

( * ) Notice: Subject to any disclaimer, the term of this patent is extended or adjusted under 35 U.S.C. 154(b) by 177 days.

(21) Appl. No.: 12/328,058

(22) Filed: Dec. 4, 2008

(65) Prior Publication Data

US 2009/0287113 A1 Nov. 19, 2009

Related U.S. Application Data

(60) Provisional application No. 61/052,823, filed on May 13, 2008.

(51) Int. Cl.
*A61B 10/00* (2006.01)
(52) U.S. Cl. ............... 600/567; 600/564; 600/562
(58) Field of Classification Search .......... 600/562–584; 606/167
See application file for complete search history.

(56) References Cited

U.S. PATENT DOCUMENTS

| | | | |
|---|---|---|---|
| 4,763,668 A * | 8/1988 | Macek et al. ............... | 600/564 |
| 5,715,832 A * | 2/1998 | Koblish et al. ............. | 600/564 |
| 5,840,044 A * | 11/1998 | Dassa et al. ............... | 600/567 |
| 5,971,940 A * | 10/1999 | Baker et al. ............... | 600/567 |
| 7,775,989 B2 * | 8/2010 | Nakao ....................... | 600/564 |
| 2005/0049520 A1 * | 3/2005 | Nakao ....................... | 600/562 |

* cited by examiner

*Primary Examiner* — Jeffrey G Hoekstra
(74) *Attorney, Agent, or Firm* — Bourque and Associates, PA

(57) ABSTRACT

Reusable biopsy forceps having a handle located at the proximal end and an end jaw assembly located at the distal end. The handle and jaw assembly are connected by a flexible catheter tube. The handle includes a handle body, fluid inlet assembly, and catheter tube coupling. The jaw assembly consists of a housing composed of a first and second portion, which holds a pair of opposed jaws and a distal actuator. The distal actuator is connected to the handle by an operating cable located inside the catheter tube. The handle controls the jaws and contains a flush port to sterilize the interior of the catheter tube and the end jaw assembly. The reusable biopsy forceps may contain a locking mechanism that is attached to the arms of the biopsy forceps handle in order to aid in taking tissue samples.

14 Claims, 4 Drawing Sheets

REUSABLE BIOPSY FORCEPS

CROSS-REFERENCE TO RELATED APPLICATIONS

This application is related to and claims priority from U.S. Provisional Application No. 61/052,823 filed on May 13, 2008 entitled Reusable Biopsy Forceps, which is incorporated fully herein by reference.

TECHNICAL FIELD

The present invention relates to reusable biopsy forceps and more particularly, relates to an improved biopsy forceps device with a flush port, removable catheter tube and/or jaw assembly, and different size jaws.

BACKGROUND INFORMATION

Biopsy forceps are used to obtain tissue samples from a particular site in a patient's body for analysis. Such samples can be taken from the heart, stomach, lungs and the like. Typical biopsy forceps include a long flexible catheter tube having a pair of opposed jaws at a distal end and a handle at the proximal end. The physician can manipulate the handle to open and close the jaws.

In order to take a tissue sample from a patient, the physician must insert the catheter tube into a guide sheath which has previously been inserted into one of the patient's vessels. Next, the biopsy forcep's distal end is inserted into the guide sheath, which then guides it into the patient's vessel. From the patient's vessel the physician can direct the catheter tube to the site the physician wishes to biopsy. Once the catheter tube is directed to the biopsy site the physician can control the jaws using the handle, which remains outside the patient's body. By using the handle, the physician can open and close the jaws of the device in order to take a tissue sample. Once the tissue sample has been taken the physician must keep the jaws in a closed position to remove the sample from the patient's body. Once the sample has been removed from the patient's body it can then be examined.

When taking a tissue sample there is an ideal amount of tissue that is needed in order to perform the necessary testing. In order to prevent either too much tissue from being taken or not enough tissue from being taken in order to perform the testing varying size jaws are available. If too much tissue is taken from the biopsy site then there is a risk that the organ could be completely perforated or that so little tissue could be left after biopsy that it could rip or tear. If not enough tissue is taken from the biopsy site then the physician will have to perform multiple biopsies, which increases the risks to the patient and could also lead to perforation, ripping or tearing of the patient's organ. Therefore, certain biopsy forceps come in varying size jaws to enable the physician to take the appropriate size tissue sample for the organ being biopsied.

Once the physician has taken a tissue sample, the biopsy forceps must be cleaned before they can be used on the next patient. When a tissue sample is taken with inseparable biopsy forceps, the interior of the biopsy forceps becomes soiled. The soaking method of sterilization does not sufficiently clean the inseparable biopsy forceps because material gets caught in the interior of the biopsy forceps and soaking does not remove it.

To ensure adequate cleaning of the biopsy forceps new forceps were developed enabling replacement of the flexible catheter tube and end jaw assembly and the sterilization of the handle after every use. Replacement of the catheter tube and jaw assembly ensures that each patient has clean biopsy forceps because it eliminates the problem of the interior of the biopsy forceps being soiled. However, by replacing the catheter tube and jaw assembly for every biopsy that is performed, excessive medical waste is created. To eliminate the excessive medical waste problem, reusable biopsy forceps were improved to enable easier cleaning with cleansing ports.

In order to sufficiently sterilize the inseparable biopsy forceps a method was developed to flush out the interior of the catheter tube and jaw assembly of the forceps. This method involves flushing out the instrument's interior with a cleansing fluid by injecting the fluid through an inlet under enough pressure to dislodge any material that has been left inside the biopsy forceps during the taking of a tissue sample.

Also, once biopsy forceps are used they must either be replaced or refurbished in order to ensure that the jaws remain sharp enough to take another tissue sample. Some biopsy forceps have been developed with replaceable end jaw assemblies. Others have been developed that are replaceable where the catheter tube and handle meet, thereby replacing both the catheter tube and jaw assembly together. Still other biopsy forceps enable a physician to replace either the catheter tube or the jaw assembly or both. By enabling replacement of either or both the catheter tube and jaw assembly the biopsy forceps can be used longer by allowing for only replacement of the worn out part rather than completely replacing the biopsy forceps.

In addition to needing to be cleaned, reusable biopsy forceps must be refurbished as they get worn down to ensure they remain sharp enough to take a tissue sample. As biopsy forceps become dull there is an increased chance that using them could cause tearing or ripping of the patient's tissue. Initially to sharpen the jaws of the biopsy forceps conventional machining methods were used, however these methods often resulted in the jaw edges that were rough and not ideal for taking tissue samples. Later methods were developed to sharpen the jaws of the biopsy forceps using a chemical solution and a power supply. This electrosharpening method sharpens the jaws by delivering an electric current to the jaws in a chemical solution and removes any imperfections in the jaws edges leaving sharpened edges.

However, biopsy forceps have not yet combined an interior cleaning method with replaceable catheter tube or jaw assembly. Accordingly, what is needed are biopsy forceps with the means for replacement of the catheter tube and/or jaw assembly and an interior cleaning method. In combining both replaceable catheter tubes and/or jaw assemblies with an interior cleaning method the replacement frequency of biopsy forceps will decrease.

SUMMARY

The present invention features reusable biopsy forceps combining a means for interior cleaning with replaceable catheter tubes and/or end jaw assemblies. The reusable biopsy forceps contain a flush port for cleaning the interior of the catheter tube and end jaw assembly and the means for replacing the catheter tube and/or end jaw assembly.

The biopsy forceps of the present invention contain a proximal end and a distal end. At the proximal end there is a handle composed of a handle body, hinge, fluid inlet assembly, and catheter tube coupling. At the distal end there is a jaw assembly composed of an opposed pair of jaws, a jaw housing, which holds and controls the jaws, and a jaw assembly coupling.

The handle at the proximate end and the jaw assembly at the distal end are connected by a catheter tube. A catheter tube coupling provides the means for attaching the catheter tube to the handle, while a jaw assembly coupling provides the means for attaching the end jaw assembly to the catheter tube. Since the biopsy forceps contain coupling systems this enables the catheter tube and/or jaw assembly to be removed and replaced when they get worn out and are no longer ideal for taking a tissue sample.

The interior of the catheter tube contains the means for controlling the jaw assembly with the handle. The operation of the hinged handle enables the jaws located at the distal end to be opened and closed. The jaws can be held in the closed position by the physician squeezing and holding the finger loops together, or using the forceps that contain the handle locking mechanism. When using the forceps with the locking mechanism, the physician squeezes the finger loops and the handle locking mechanism engages to keep the forceps' jaws in the closed position without the need to hold any pressure on the finger loops.

Also located on the handle is a flush port system composed of a fluid inlet tube and fluid inlet cap. The flush port system is used for cleaning the interior of the catheter tube and end jaw assembly. The fluid inlet cap enables a container to be attached to the biopsy forceps to inject a cleaning solution through the fluid inlet tube into the inner tube member of the catheter tube. The cleaning solution should be pressurized when injected through the fluid inlet cap to dislodge any biologics that may have gotten into the interior of the catheter tube and end jaw assembly.

It is important to note that the present invention is not intended to be limited to a system or method, which must satisfy one or more of any stated objects or features of the invention. It is also important to note that the present invention is not limited to the preferred, exemplary, or primary embodiment(s) described herein. Modifications and substitutions by one of ordinary skill in the art are considered to be within the scope of the present invention.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENTS

Figure 1:
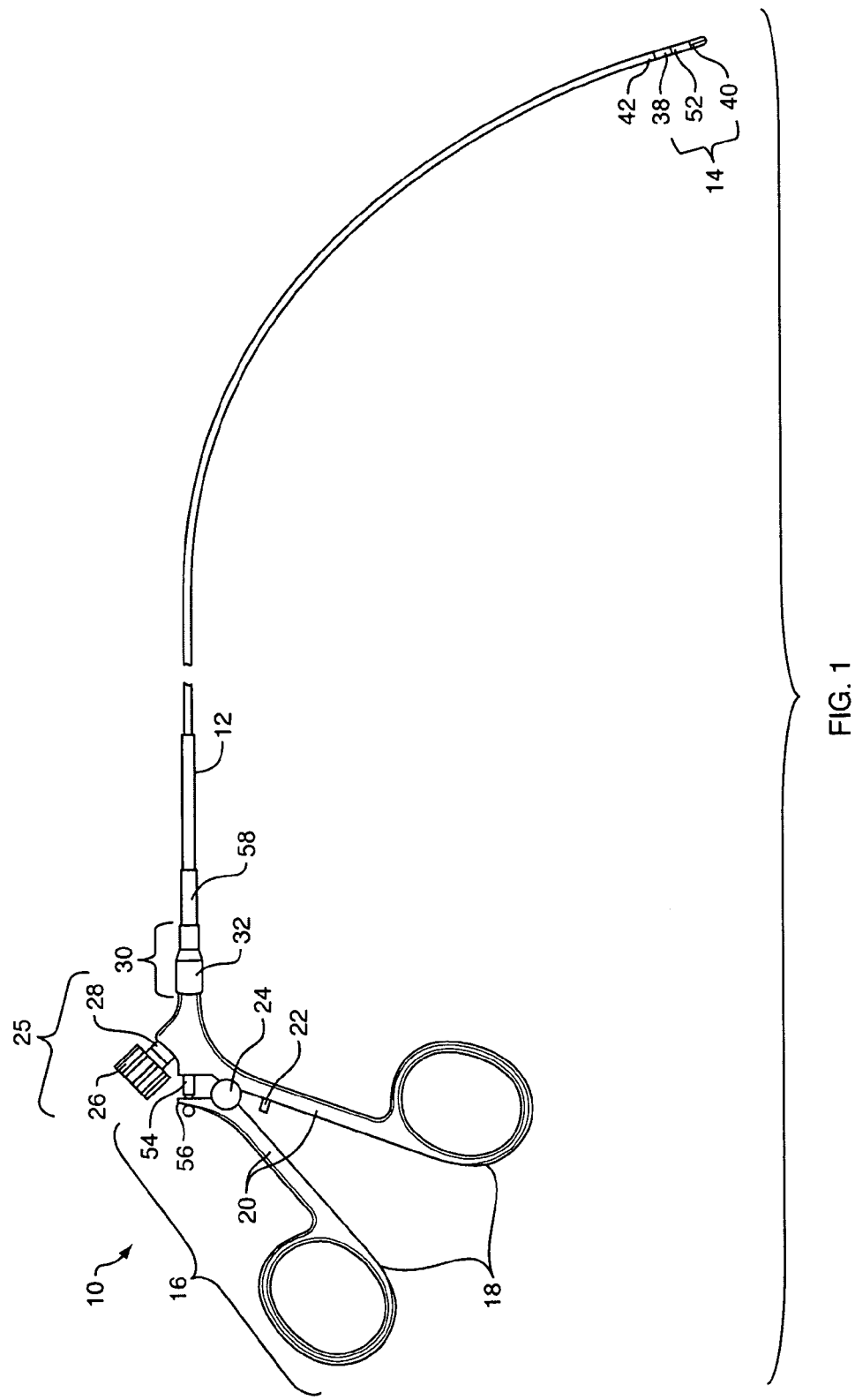
FIG. 1 is a perspective view of the reusable biopsy forceps with flush port in accordance with the present invention.
Figure 2:
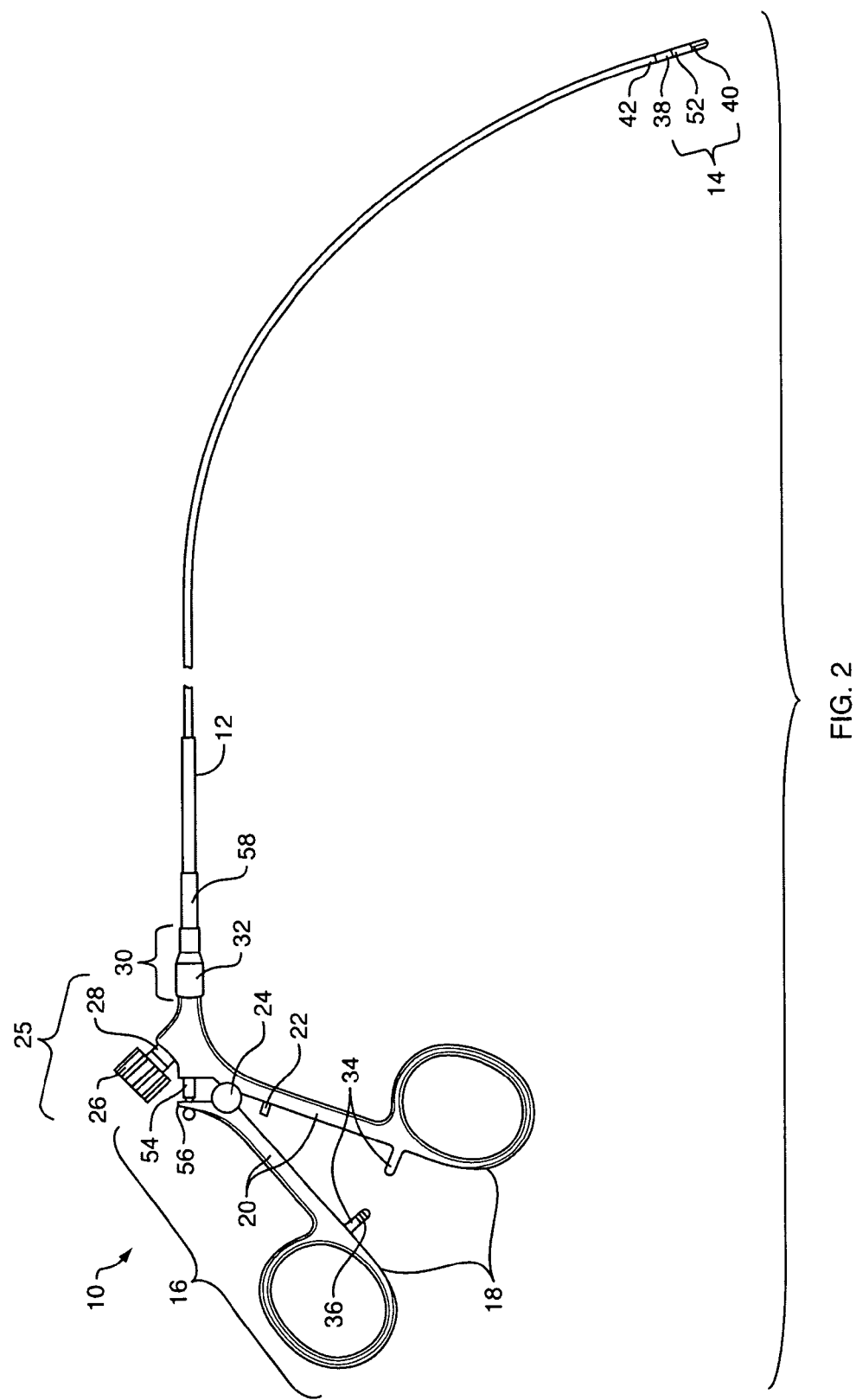
FIG. 2 is a perspective view of the reusable biopsy forceps with a toothed locking mechanism and flush port in accordance with the present invention.
Figure 3:
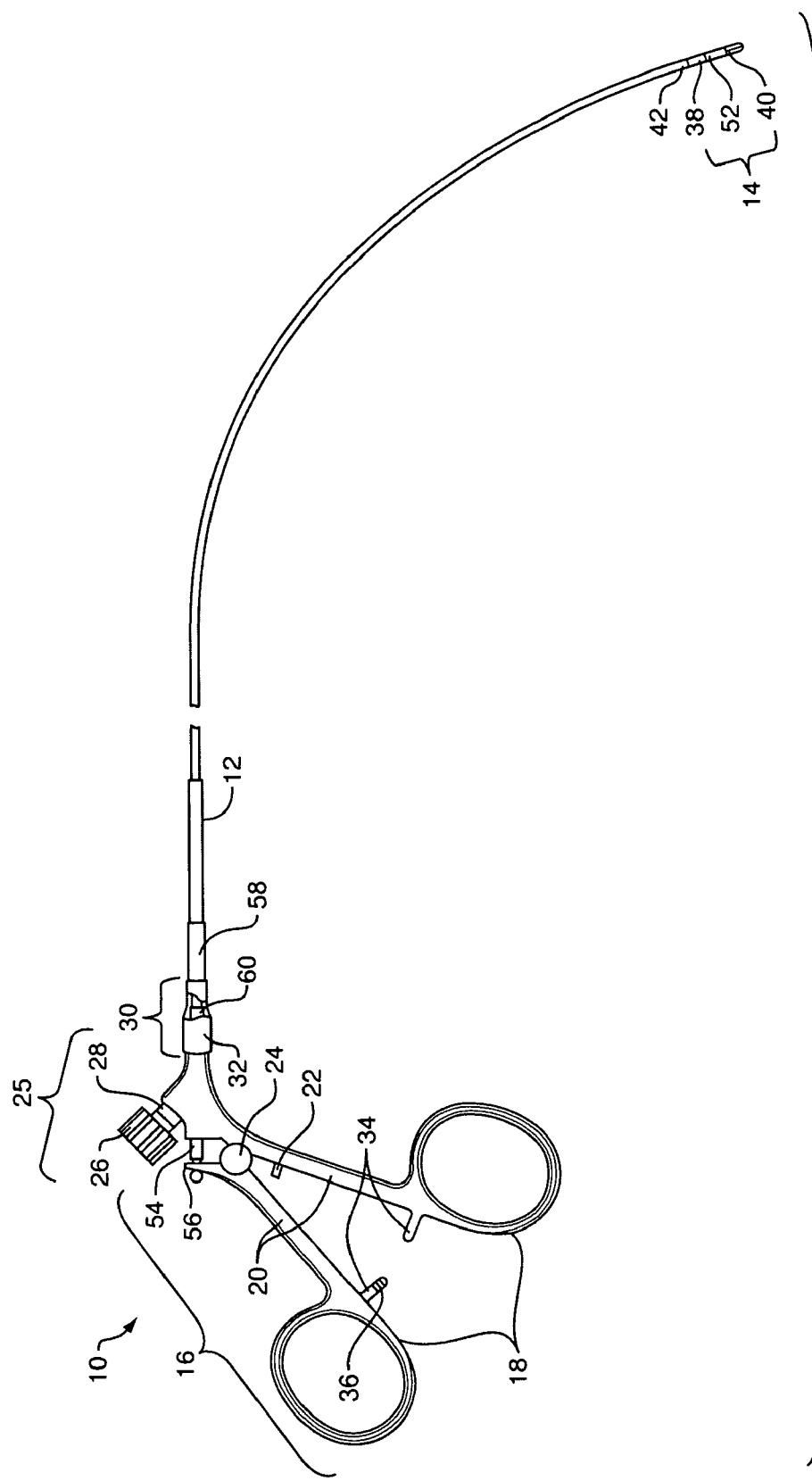
FIG. 3 is a perspective view of the reusable biopsy forceps in accordance with the present invention with a toothed locking mechanism and flush port showing the catheter tube locking mechanism.
Figure 4:
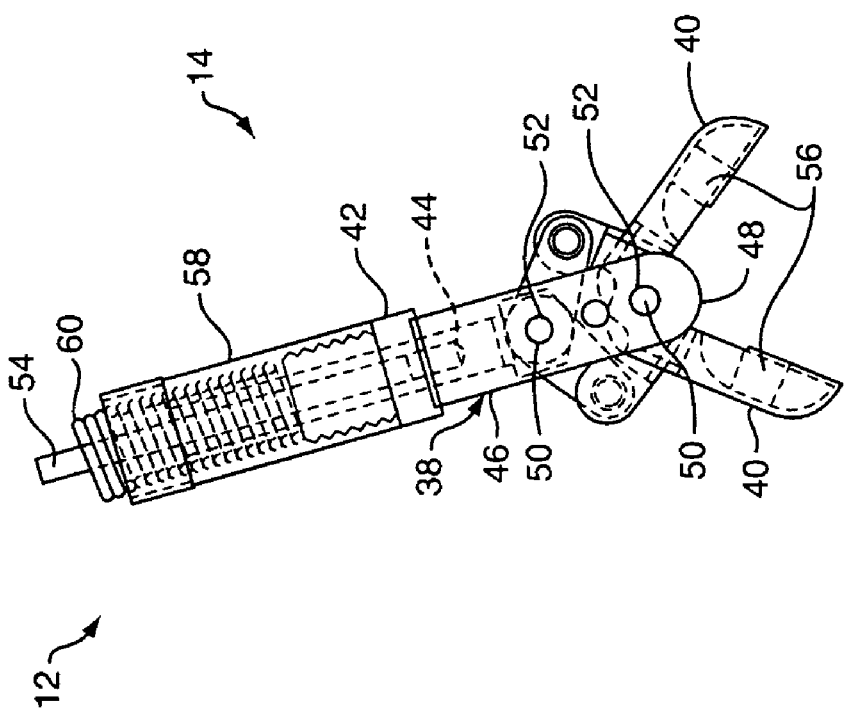
FIG. 4 is see-through side view of the end jaw assembly of the reusable biopsy forceps according to the present invention.

The present invention is directed to reusable biopsy forceps 10, FIG. 1, with a flush port system and a coupling system for replacement of the catheter tube 12 and/or end jaw assembly 14. The biopsy forceps 10 are composed of a flexible catheter tube 12, an end jaw assembly 14, and a handle 16.

Handle 16 is composed of finger loops 18, two arms 20, a stop screw 22, a hinge 24, a fluid inlet assembly 25, and a catheter tube coupling system 30. The catheter tube coupling system 30 contains a coupling nut 32 to tighten catheter tube 12 onto handle 16. The body of handle 16 is composed of two finger loops 18 located at the proximal end of handle 16. Extending from finger loops 18 are two arms 20 which intersect at hinge 24 to create a pivot for opening and closing jaws 40. Stop screw 22 is located on one of arms 18 to prevent the physician from over extending jaws 40 when squeezing handle 16. The other arm 18 contains a hole 56 at the distal end to secure operating cable 54 to handle 16 to enable handle 16 to control jaws 40. Fluid inlet assembly 25 is composed of a fluid inlet cap 26 and a fluid inlet tube 28. Fluid inlet cap 26 enables fluid to be injected into the interior of biopsy forceps 10 through fluid inlet tube 28. In addition, one embodiment of reusable biopsy forceps 10 contains a locking mechanism 34 on handle 16 with interlocking teeth 36 to secure handle 16 into a locked position.

Jaw assembly 14 is composed of a housing 38, a pair of opposed jaws 40, a jaw assembly coupling 42, and a distal actuation member 44. Housing 38 is composed of a first portion 46 and a second portion 48 to secure jaws 40, jaw assembly coupling 42, and distal actuation member 44 into place. First portion 46 contains slots 50 and second portion 48 contains pins 52, which interlock in slots 50 to secure housing 38. Jaws 40 are secured to housing 38 and attached to distal actuation member 44, which enables jaws 40 to open and close. Distal actuation member 44 is attached to catheter tube 12 through jaw assembly coupling 42. Jaw assembly coupling 42 is the interaction where catheter tube 12 is inserted into housing 38 of jaw assembly 14. The operating cable 54, which travels through catheter tube 12, is attached to distal actuation member 44 to operate jaws 40. The interior of jaws 40 contains cups 56 to hold the tissue sample after it has been taken from the patient. Since, various size tissue samples are needed depending on the organ being biopsied jaws 40 come in various sizes. With varying sized jaws 40 a physician can choose the correct size to ensure that only one sample needs to be taken. By taking only one tissue sample, the risk of harm to the patient decreases. The physician is also aided in ensuring that only one tissue sample needs to be taken by jaws 40 opening to a minimum of 80 degrees. The minimum opening of 80 degrees allows a physician to more easily position jaws 40 around the tissue site to ensure an ample sample is taken.

Catheter tube 12 is composed of an outer tube member 58 and an inner tube member 60. An operating cable 54 is contained inside of inner tube member 60. Operating cable 54 connects handle 16 to jaw assembly 14 enabling the movements of finger loops 18 to control jaws 40 and open and close jaws 40. Catheter tube 12 is also connected to fluid inlet tube 28 through catheter tube coupling 30. Thereby allowing a cleaning fluid injected into fluid inlet cap 26 to flow through fluid inlet tube 28 into inner tube member 60 of catheter tube 12 and finally through end jaw assembly 14 to sterilize the interior of the biopsy forceps 10.

The preferred method of cleaning biopsy forceps 10 after they are used to take a patient's tissue sample is to sterilize the interior and exterior of the forceps 10. The interior of biopsy forceps 10 should be flushed out using a cleansing solution. To accomplish this, a container of cleansing and sterilizing solution should be attached to fluid inlet cap 26. The cleansing solution should then be released and pushed through fluid inlet tube 28, then inner tube member 60 of catheter tube 12 and finally out of the interior of biopsy forceps 10 through jaw assembly 14. The cleansing fluid should be pressurized as it travels through the interior of biopsy forceps 10 to dislodge any biologics left after a biopsy has been performed. Once the interior of biopsy forceps 10 has been sterilized, the exterior must be sterilized. Handle 16, outer tube member 58 of catheter tube 12, the exterior of end jaw assembly 14, and jaws 40 should be sterilized using known methods.

The preferred life expectancy of end jaw assembly 14 of reusable biopsy forceps 10 is five or six refurbishments. As discussed above, a refurbishment involves the re-sharpening of the edges of jaws 40. To make re-sharpening easier jaw assembly 14 is removable and replaceable. Once jaw assembly 14 has been used and refurbished five or six times it should be disposed of and a new end jaw assembly 14 should be attached and used. When necessary catheter tube 12 can also be replaced by loosening coupling nut 32 and disconnecting operating cable 54 from its connection at catheter tube coupling 30 with handle 16 and its connection at jaw assembly coupling 42 with distal actuation member 44 of jaw assembly 14. Catheter tube 12 can either be replaced in conjunction with jaw assembly 14 or independently of jaw assembly 14. The combination of the improved interior cleaning method and the means for replacement of catheter tube 12 and/or jaw assembly 14 increases the life expectancy of biopsy forceps 10. Therefore this combination decreases the amount of biomedical waste and reduces the cost of biopsy forceps.

Modifications and substitutions by one of ordinary skill in the art are considered to be within the scope of the present invention, which is not to be limited except by the following claims. As mentioned above, the present invention is not intended to be limited to a system or method which must satisfy one or more of any stated or implied objectives or features of the invention and should not be limited to the preferred, exemplary, or primary embodiment(s) described herein. The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention which is not to be limited except by the allowed claims and their legal equivalents.

The invention claimed is:

1. A biopsy forceps device comprising:
a flexible catheter tube having a proximal end and a distal end, wherein said flexible catheter includes an outer tube member, an inner tube member disposed within said outer tube member, an operating member, disposed within said inner tube member and coupled to a handle portion and an end jaw assembly, said operating member configured for translational movement within said outer tube, and an inner region between said inner tube member and said outer tube member;
a handle at said proximal end of said tube, said handle including a handle body with two finger loops and two arms, a hinge configured for pivotally connecting said two arms, a fluid inlet assembly, and a catheter tube coupling, said fluid inlet assembly including a fluid inlet configured for receiving a cleaning and sterilizing fluid and a fluid inlet tube in fluid communication with said inner region between said inner tube member and said outer tube member of said catheter tube, said fluid inlet assembly in fluid communication with said inner region of said catheter tube, for introducing said cleaning and sterilizing fluid into said catheter tube inner region to sterilize and clean said inner region of said catheter tube;
an end jaw assembly at said distal end of said tube, said end jaw assembly including a pair of opposed end jaws operable between an open position and a closed position in response to said translational movement of said operating member, said pair of opposed end jaws pivotable about an axis that is fixed without any translational movement in a longitudinal direction; and
a first opening at said distal end of said handle, for securing said catheter tube inside of said catheter tube coupling.

2. The biopsy forceps of claim 1, wherein said catheter tube and said end jaw assembly are permanently affixed.

3. The biopsy forceps of claim 2, wherein said opposed jaws open to a minimum of 80 degrees.

4. The biopsy forceps of claim 3, wherein said opposed jaws are replaceable with different sized jaws.

5. The biopsy forceps of claim 3, wherein said handle contains a teeth-bearing locking mechanism which enables said opposed jaws to be locked in said closed position.

6. The biopsy forceps of claim 1, wherein said catheter tube and said end jaw assembly are detachable.

7. The biopsy forceps of claim 6, wherein said opposed jaws open to a minimum of 80 degrees.

8. The biopsy forceps of claim 7, wherein said opposed jaws are replaceable with different sized jaws.

9. The biopsy forceps of claim 8, wherein said handle contains a teeth-bearing locking mechanism which enables said opposed jaws to be locked in said closed position.

10. A biopsy forceps device comprising:
a flexible catheter tube having a proximal end and a distal end, wherein said flexible catheter includes an outer tube member, an inner tube member disposed within said outer tube member, an operating member, disposed within said inner tube member and coupled to a handle portion and an end jaw assembly, said operating member configured for translational movement within said outer tube, and an inner region between said inner tube member and said outer tube member;
a handle at said proximal end of said tube, said handle including a handle body with two finger loops and two arms, a hinge configured for pivotally connecting said two arms, a fluid inlet assembly, and a catheter tube coupling, said fluid inlet assembly including a fluid inlet configured for receiving a cleaning fluid and a fluid inlet tube in fluid communication with said inner region of said catheter tube, for introducing said cleaning fluid into said inner region of said catheter tube under pressure to sterilize and clean said inner region of said catheter tube;
an end jaw assembly at said distal end of said tube, said end jaw assembly including a pair of opposed end jaws operable between an open position and a closed position in response to said translational movement of said operating member, said pair of opposed end jaws pivotable about an axis that is fixed without any translational movement in a longitudinal direction;
a first opening at said distal end of said handle for securing said catheter tube inside of said catheter tube coupling; and
a second opening at said distal end of said catheter tube for securing said end jaw assembly to said catheter tube.

11. The biopsy forceps of claim 10, wherein said opposed jaws open to a minimum of 80 degrees.

12. The biopsy forceps of claim 11, wherein said opposed jaws come in different sizes.

13. The biopsy forceps of claim 12, wherein said handle contains a teeth locking mechanism which enables said opposed jaws to be locked in said open position.

14. A biopsy forceps device comprising:

a flexible catheter tube having a proximal end and a distal end, wherein said flexible catheter includes an outer tube member and an inner tube member disposed within said outer tube member, an operating member, disposed within said inner tube member and coupled to a handle portion and an end jaw assembly, said operating member configured for translational movement within said outer tube, and an inner region between said inner tube member and said outer tube member;

a handle portion at said proximal end of said tube, said handle portion including a handle body with two finger loops and two arms, a hinge configured for pivotally connecting said two arms, a fluid inlet assembly, and a catheter tube coupling, said fluid inlet assembly including a fluid inlet configured for receiving a cleaning and sterilizing fluid and a fluid inlet tube in fluid communication with said inner region of said catheter tube, said fluid inlet assembly providing fluid communication with said inner region of said catheter tube, for introducing said cleaning and sterilizing fluid into said catheter tube to sterilize and clean said tube member of said catheter tube;

an end jaw assembly at said distal end of said tube, said end jaw assembly including a pair of opposed end jaws operable between an open position and a closed position; and a first opening at said distal end of said handle, for securing said catheter tube inside of said catheter tube coupling.

* * * * *